United States Patent
Shaw et al.

(10) Patent No.: US 6,494,863 B1
(45) Date of Patent: Dec. 17, 2002

(54) ONE-USE RETRACTING SYRINGE WITH POSITIVE NEEDLE RETENTION

(75) Inventors: Thomas J. Shaw, Little Elm; Judy Zhu, Plano, both of TX (US)

(73) Assignee: Retractable Technologies, Inc., Little Elm, TX (US)

(*) Notice: Subject to any disclaimer, the term of this patent is extended or adjusted under 35 U.S.C. 154(b) by 0 days.

(21) Appl. No.: 09/978,906

(22) Filed: Oct. 15, 2001

(51) Int. Cl.[7] .................................................. A61M 5/00
(52) U.S. Cl. ...................................... 604/110; 604/220
(58) Field of Search ............................... 604/110, 220, 604/218, 236, 238, 181, 187

(56) References Cited

U.S. PATENT DOCUMENTS

| | | | |
|---|---|---|---|
| 4,961,728 A | 10/1990 | Kosinski | 604/110 |
| 4,973,310 A | 11/1990 | Kosinski | 604/110 |
| 5,000,737 A | 3/1991 | Free et al. | 604/110 |
| 5,205,825 A | 4/1993 | Allison et al. | 604/110 |
| 5,385,551 A | 1/1995 | Shaw | 604/110 |
| 5,531,691 A | 7/1996 | Shonfeld et al. | 604/110 |
| 5,562,623 A | 10/1996 | Shonfeld et al. | 604/110 |
| 5,578,011 A | 11/1996 | Shaw | 604/110 |
| 5,632,733 A | 5/1997 | Shaw | 604/195 |
| 6,015,438 A | 1/2000 | Shaw | 624/195 |
| 6,090,077 A | 7/2000 | Shaw | 604/195 |
| 6,273,870 B1 * | 8/2001 | Garvin | 604/110 |
| 6,344,031 B1 * | 2/2002 | Novacek et al. | 604/110 |

* cited by examiner

*Primary Examiner*—Sharon Kennedy
(74) *Attorney, Agent, or Firm*—Locke Liddell & Sapp LLP; Monty L. Ross

(57) ABSTRACT

A retracting syringe of one use has a plunger comprising a handle portion and a needle retention portion forward of the handle portion. A positive locking structure in the syringe barrel ensures the syringe is not reused. In one embodiment, the positive locking structure is a stop in the syringe barrel. The handle portion separates after one use and is removed from the syringe. In a second embodiment, the handle portion has a plurality of stepped serrations and the positive locking structure is a clip which is movable with respect to both the handle portion and the barrel. In a third embodiment, the positive locking structure is a clip fixed in an enlarged back opening of the barrel with springing points which are protected from a plurality of stepped serrations on the handle portion by a sliding collar. This one use feature can be applied to a nonretracting syringe.

35 Claims, 9 Drawing Sheets

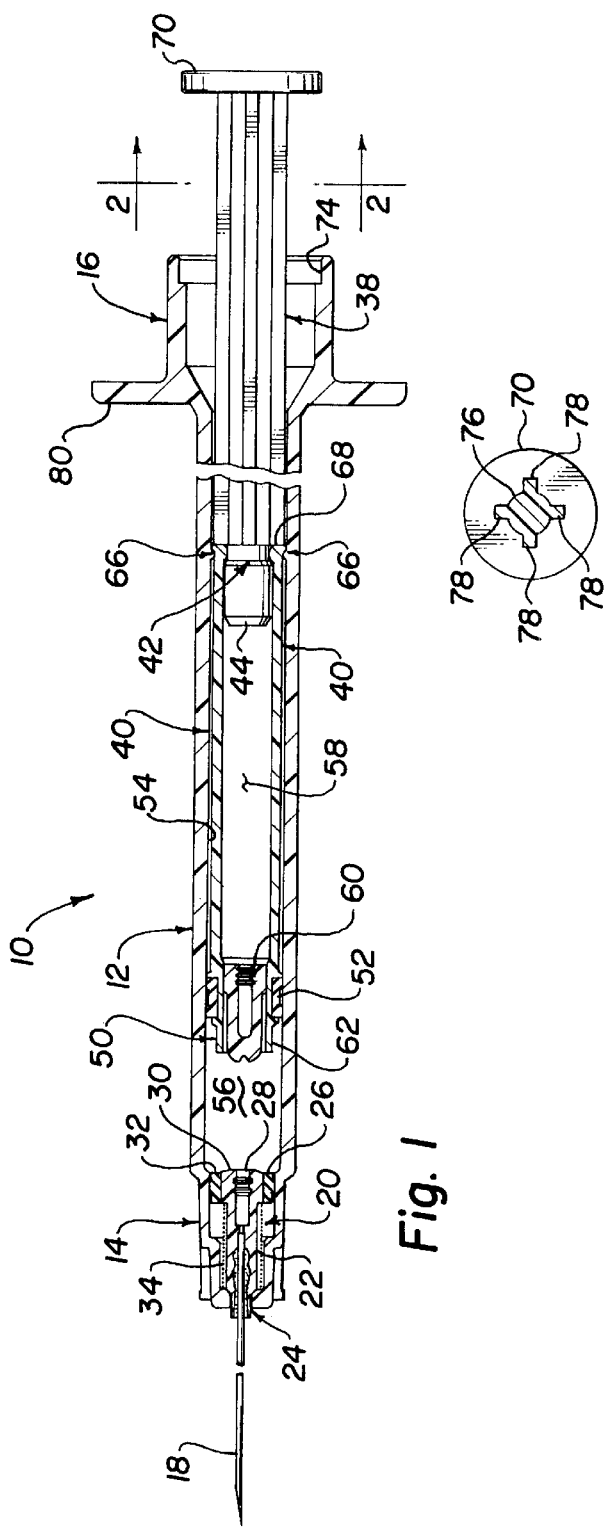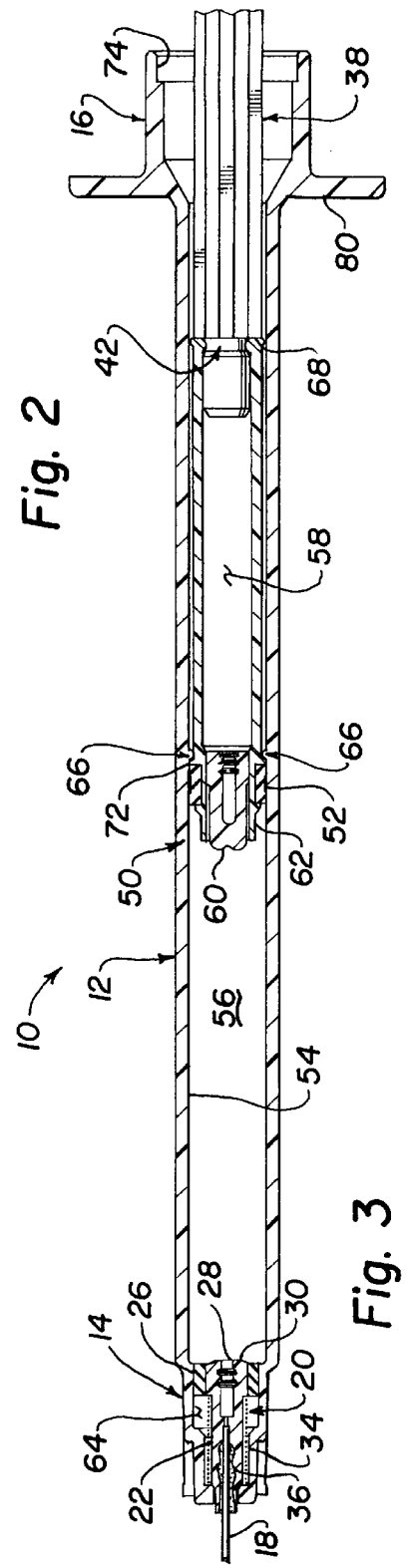

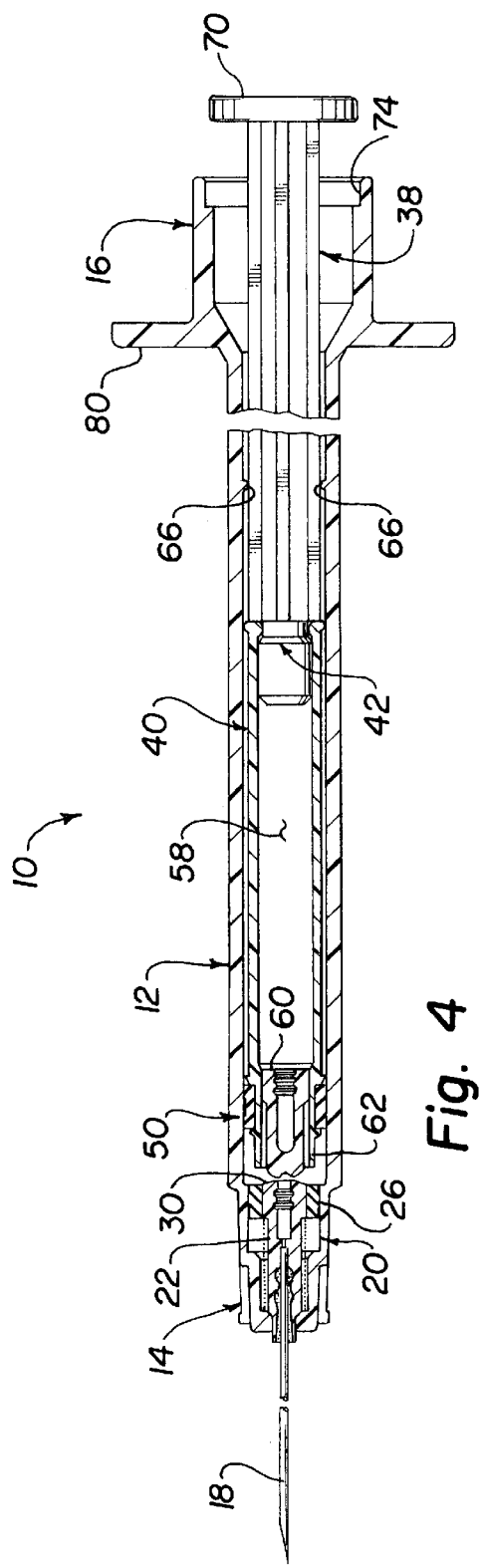
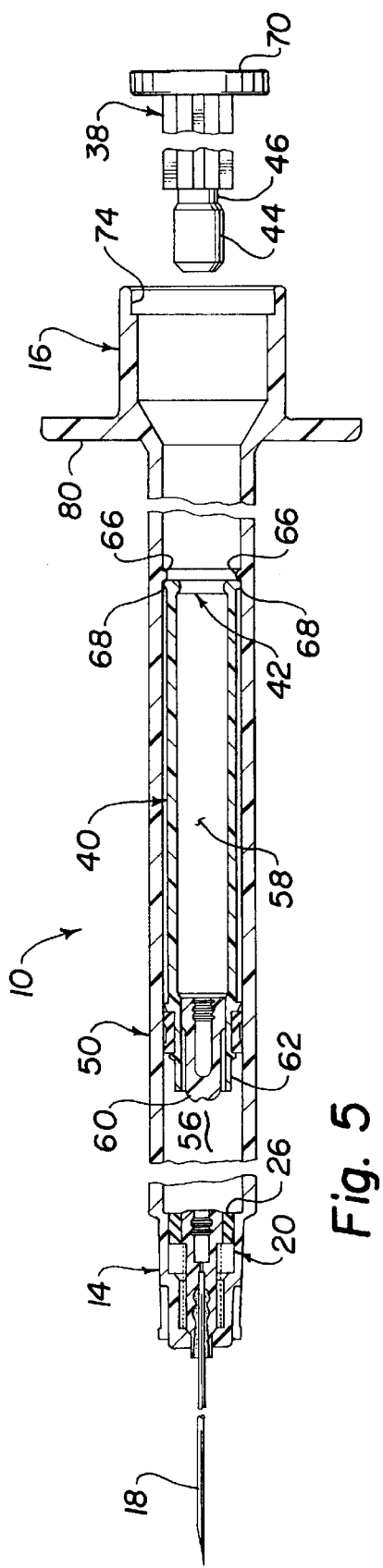
Fig. 4
Fig. 5

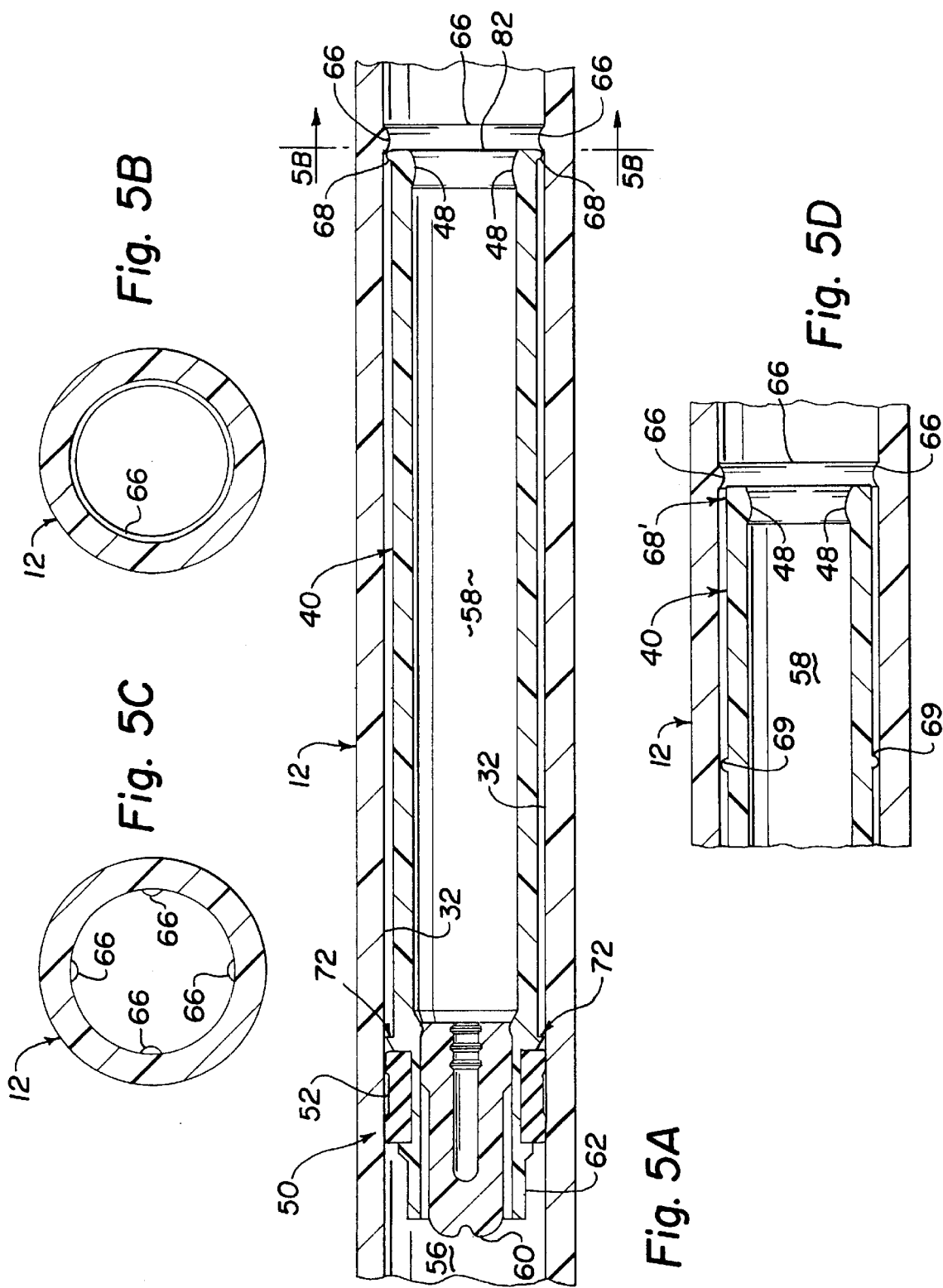

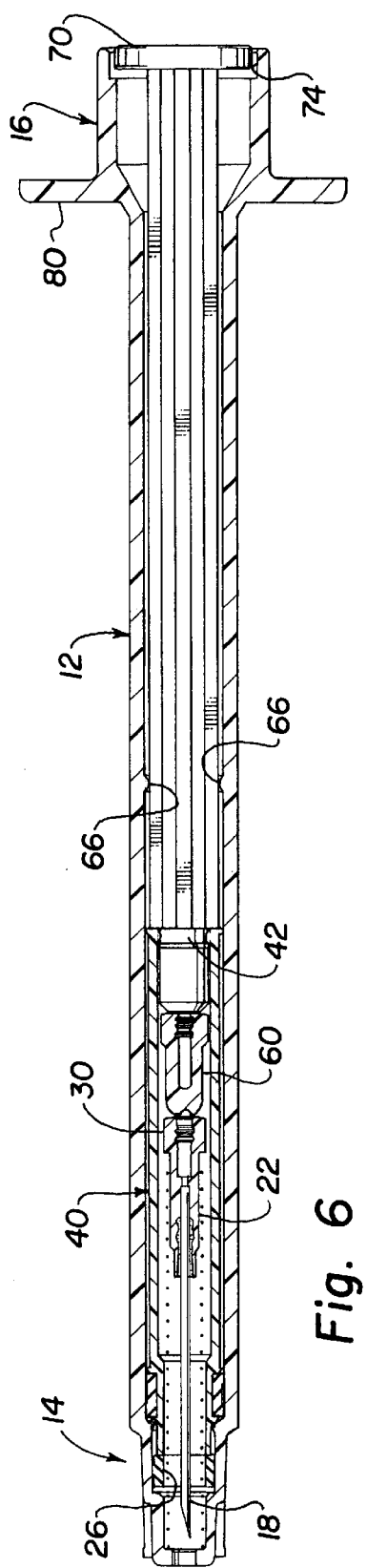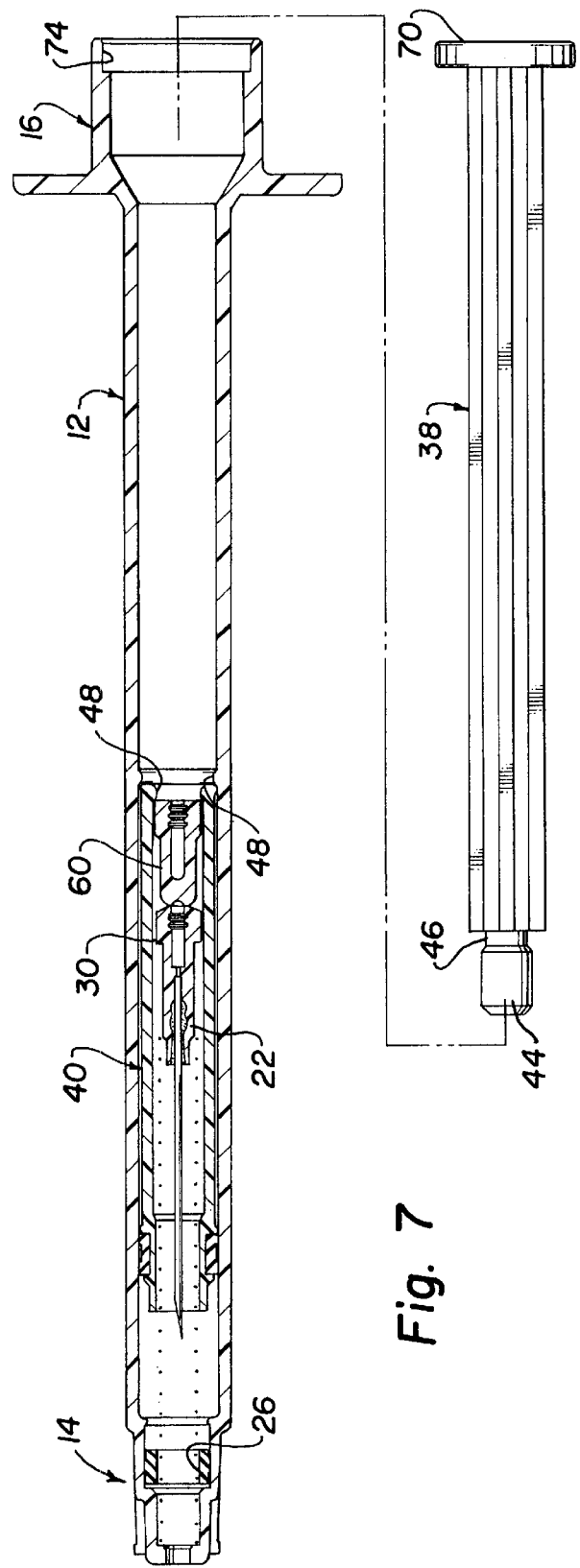
Fig. 6
Fig. 7

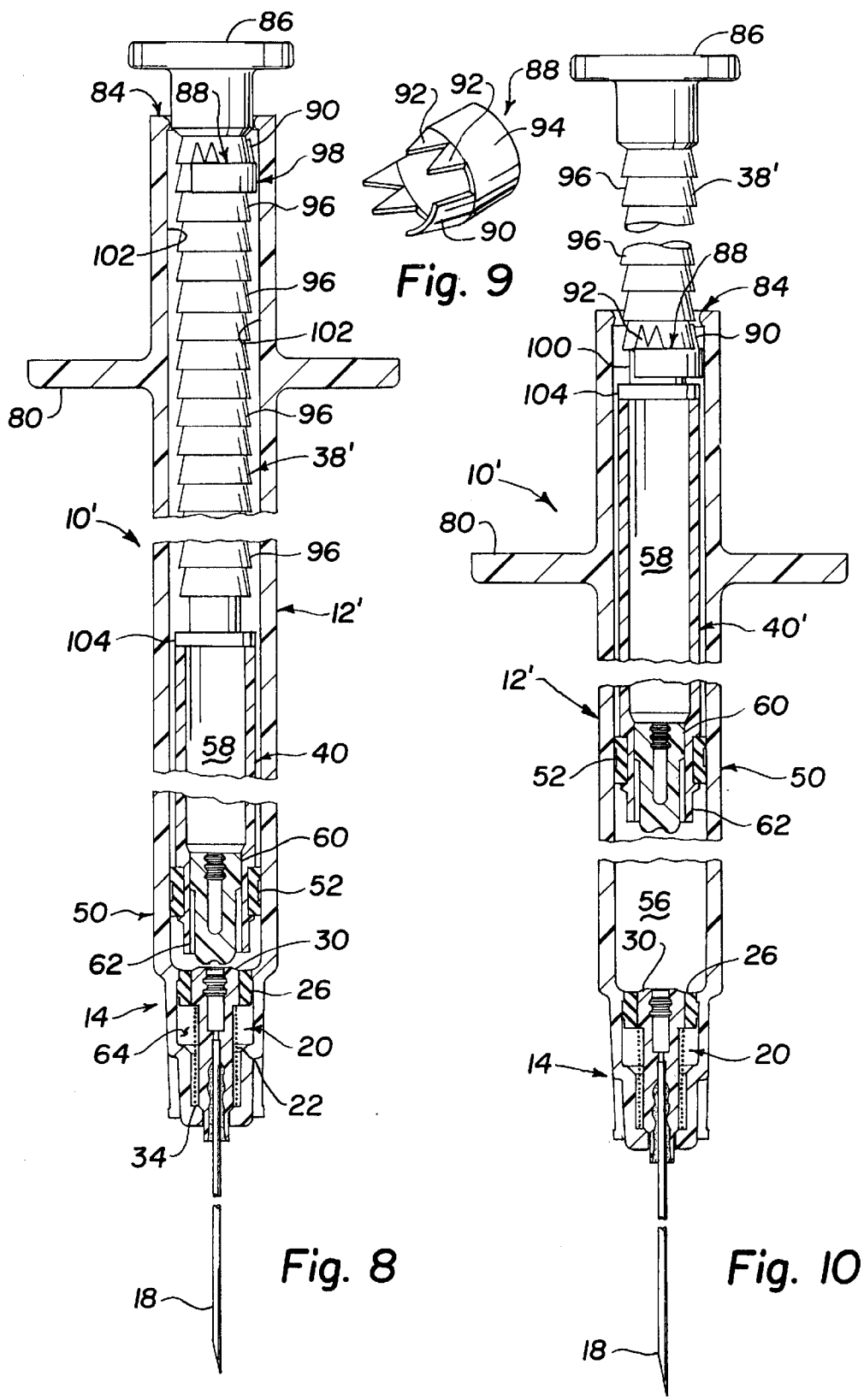

ONE-USE RETRACTING SYRINGE WITH POSITIVE NEEDLE RETENTION

BACKGROUND OF THE ART

1. Field of the Invention

The invention pertains to medical devices for fluids, more particularly syringes with a retractable needle which cannot be reused after an injection has been made.

2. Background of the Prior Art

They syringe art has advanced rapidly in recent years because of the threat of AIDS and other infectious diseases and the inevitability of accidental needle sticks suffered by healthcare providers from the use of needles on infected patients. Used syringes with extended needles present a risk to medical personnel, sanitation employees and others in the disposal chain. The prior art has disclosed a large number of syringes and other medical devices with retractable needles, usually retracting into the barrel or into a needle receiving chamber within the syringe barrel. The most advanced of the retracting syringes are disclosed in our U.S. Pat. Nos. 5,385,551; 5,578,011; 5,632,733; 6,015,438; and 6,090,077, which are all hereby incorporated herein by reference. The syringes disclosed in the foregoing patents are retracted automatically by continued pushing on the plunger handle while an injection is being finished and offer one handed handling and retraction of the syringe so that the healthcare worker never needs to be exposed to a contaminated needle. Plunger actuated automatic retraction of these devices takes place before the needle is removed from the patient. These retractable syringes are suitable for mass production at low cost with a high degree of reliability and repeatability of operation. They are suited to automated production of parts and automated assembly in a number of different barrel sizes, needle sizes and for different uses.

While the syringes described above and other retractable syringes have eliminated or substantially reduced the needle stick problem, some have expressed a need for syringes of one-use which cannot be reused under any circumstances. Most, if not all, retractable syringes require the user to take some action to initiate retraction of the needle after an injection has been made. This leaves the retractable syringe open for a possible reuse if the user fails to retract the needle after one use. A solution to this problem has been proposed in the case of nonretractable syringes by means of various devices which mechanically lock the plunger handle after the first use of the syringe, but none of these devices have a retractable needle. Therefore, the needle remains exposed with the continued potential for needle sticks even though the syringe cannot be reused because the plunger cannot be withdrawn a second time. Examples of syringes with locking plunger handles but which do not retract, include Free et al., U.S. Pat. No. 5,000,737, entitled "Single Use Disposable Syringe"; Allison et al., U.S. Pat. No. 5,205,825, entitled "Insertable Element for Preventing Reuse of Plastic Syringes"; Kosinski, U.S. Pat. No. 4,973,310, entitled "Single-Use Syringe"; Kosinski, U.S. Pat. No. 4,961,728, entitled "Single-Use Syringe having Misuse Resistant Features"; Shonfeld et al., U.S. Pat. No. 5,531,691, entitled "Single Use Syringe Assembly"; and Shonfeld et al., U.S. Pat. No. 5,562,623, entitled "Single-Use Syringe Assembly including Spring Clip Lock and Plunger". The disclosure of these patents is incorporated herein by reference.

The single-use syringes mentioned above cannot be reused after one injection is made, but a contaminated needle is still extended and must be capped, removed or otherwise disposed of before the syringe is rendered safe. Thus, there is a need for an improved syringe of one-use with a needle that retracts into the syringe barrel after use and which cannot be reused whether or not the needle is retracted.

SUMMARY OF THE INVENTION

The present invention is a retracting syringe of one use having a handle operated needle retention chamber which cannot be removed from the syringe barrel. The retracting feature obviates the danger associated with an exposed needle after an injection is made. The positive locking structure assures that the syringe is truly a syringe of one use and cannot be reused. In the various embodiments the movable parts comprising the handle portion and the needle retention chamber are limited in rearward movement and contained in the syringe barrel after one rearward movement of the handle to fill the syringe with fluid and one forward movement of the handle to discharge the fluid from the syringe. The invention serves to eliminate the risk that a retractable syringe, which is supposed to be retracted after one use, could possibly be reused because the operator chose to or failed to activate the retraction mechanism thereby leaving the needle exposed for a second use. This cannot occur because the positive locking structure prevents removal of the needle retention chamber by blocking its removal. The needle retention chamber is retained in the barrel whether or not the retraction mechanism is activated and whether or not the needle is retracted. This suggests that the advantage of the invention can also be applied to a nonretracting syringe where the needle is fixed in the front end of the barrel and this should be considered another aspect of the invention disclosed herein. In a nonretracting syringe, the invention works in the same way to limit or prevent withdrawal of the handle (plunger) from the barrel. If the handle cannot be drawn back a second time, the syringe cannot be refilled with fluid.

An elongated hollow syringe barrel having a front end and an open back preferably has a retractable needle retractably mounted in a retraction structure located in the front end of the syringe barrel and biased for retraction in a rearward axial direction. Movable parts comprising a handle attached to a needle retention chamber performs the function of an ordinary syringe plunger in the barrel. The front end portion of the needle retention chamber has a piston mounted in sliding sealed contact with the interior of the barrel. The movable parts are moved by means of the handle extending from the open back of the barrel. The back end portion of the handle portion has a cap for applying thumb force to the handle. The needle retention chamber has an openable sealed opening in front to receive the retracted needle into the needle retention chamber when the retraction mechanism is actuated by forward movement of the plunger after the fluid has been discharged during an injection into a patient. Retraction of the needle into the needle retention chamber is triggered by forward movement of the needle retention chamber against the retraction structure in response to movement of the handle after the injection is completed.

Positive locking structure is located within the syringe barrel to limit movement of the needle retention chamber in a rearward direction and prevent its removal from the syringe barrel after one use. The positive locking structure is adapted to have no effect on one rearward movement and one forward movement of the movable parts to the fullest extent of forward movement but subsequent movement of the needle retention chamber in a rearward direction is limited to maintain said chamber within the syringe barrel.

In the first embodiment, positive locking structure is fixed within the barrel at a fixed location. The locking structure comprises a constriction of the barrel diameter comprising a first stop while the needle retention chamber has a diametrically enlarged section comprising a second stop wherein the second stop can be forced passed the first stop in a forward direction by pressing on the handle but which resists movement in a rearward direction caused by pulling on the handle. The first embodiment further has a handle portion which is removably attached to the needle retention chamber and separable therefrom by a separation force which is less than the force required to force the second stop past the first stop in a rearward direction. The handle is preferably separable from the needle retention chamber by release of the separating parts without breaking them.

The first embodiment further preferably includes a catch on the front end portion which can be forced forward past the first stop by pressing on the handle before the second stop moves past the first stop. As long as the second stop does not move forward past the first stop, the handle can be withdrawn to fill the syringe. The catch on the front end portion of the needle retention chamber limits the amount of rearward travel of the movable parts to establish the maximum design fill volume of the syringe. The catch comes in contact with the first stop. When the plunger is depressed to make the injection, however, the second stop on the back of the needle retention chamber or some intermediate position on the needle retention chamber moves past the first stop and thereby provides the limiting feature previously described which causes a two part handle to separate when the handle is pulled to the rear. Once the handle is pushed forward with all stops beyond the first stop in the barrel, the syringe can be emptied and the retraction mechanism activated by continued forward movement of the handle.

A second embodiment of the invention has the elongated hollow syringe barrel preferably having a retractable needle retractably mounted in the retraction structure located in the front end of the syringe barrel and biased for retraction in a rearward direction. It has a movable handle in the syringe barrel having a front end portion having a piston in sliding sealed contact with the interior of the barrel, a back end portion having a cap at the back end for applying thumb force to the handle and a needle retention chamber in the front end portion of the handle for receiving the retractable needle. In the second embodiment, the positive locking structure is still located within the syringe barrel. It limits movement of the handle in a rearward direction and prevents its removal from the syringe barrel after one use. However, the locking structure moves relative to the barrel in the second embodiment.

The handle carries the locking structure which is movable in only one direction from a first position near the back of the handle to a second position nearer the front of the handle. The locking structure is adapted to positively engage the syringe barrel and limit movement of the needle retention chamber in a rearward direction after the locking structure is moved forward of the first position. The needle retention chamber is preferably located just forward of the second position of the locking structure. The handle preferably has a plurality of stepped serrations and the positive locking structure is preferably a clip having an inwardly angled tab relative to the stepped serrations which allows the clip to move forwardly on the handle while preventing the clip from moving rearwardly. The clip has at least one outwardly angled point which engages the syringe barrel to prevent withdrawal of the handle. The points simply slide along the surface of the handle because they are angled backwardly but prevent rearward movement which causes the points to dig into the inner surface of the barrel. The clip preferably circumscribes part but not all of the stepped serrations of the back end of the barrel in the form of something slightly more than a half circle shape.

A third embodiment of the invention includes all the other syringe features of the first and second embodiments except for a different positive locking structure. In the third embodiment, the positive locking structure to limit movement of the handle in a rearward direction is located within the syringe barrel in a fixed position relative to the barrel. More particularly, said structure is located inside the open back of the barrel. The structure mounted inside of the open back of the barrel in a fixed position relative to the barrel is preferably a springing clip having one or more forwardly angled points which are protected by a sliding collar carried by the handle from contacting the handle during an initial withdrawal of the handle to draw fluid into the barrel. This allows one withdrawal in the handle in a rearward direction from an initial forward position relative to the barrel without engaging the springing points with the handle. When the plunger is depressed in a forward direction, the sliding collar moves forward out of contact with the points of the springing clip whereupon the springing clip engages the handle to prevent its withdrawal. In the third embodiment, the back end portion of the handle has a plurality of stepped serrations like the second embodiment on which the sliding collar carried by the handle resides. The sliding collar has an angled surface which allows the plunger handle to move rearwardly relative to the collar but the collar has a catch which catches the edge of a stepped serration which causes it to move forward with the handle and away from the springing clip. The springing clips simply ride over the stepped serrations without interference as the handle is being moved forward but as soon as the handle is moved backward, the teeth dig into the handle and stop any rearward movement of the handle. A stop surface on the back of the needle retention chamber can contact the collar and prevent further withdrawal of the handle after the handle is pulled back to the maximum extent. The collar is trapped within the barrel.

Although the invention is most effective when combined with a retractable needle mounted in a retraction structure in the front of the syringe, the invention is primarily concerned with the issue of one use and therefore is applicable to syringes with fixed needles as well as syringes with retractably mounted needles.

BRIEF DESCRIPTION OF THE DRAWINGS

FIG. 1 is a longitudinal cross-sectional view of a first embodiment of the invention having a needle retention chamber and separable handle which is shown in the ready to fill position;

FIG. 2 is a cross-section along the lines 2—2 in FIG. 1 of the handle and thumb cap of the first embodiment;

FIG. 3 is a longitudinal cross-sectional view of the first embodiment of FIG. 1 with the plunger pulled back to a stop to the maximum fill position;

FIG. 4 is a longitudinal cross-sectional view of the syringe of the previous Figures after the handle is depressed to the end of injection position;

FIG. 5 is a longitudinal cross-sectional view of the syringe of the previous Figures showing handle disengagement if the handle is pulled back from the position of FIG. 4 to the position of FIG. 5 without initiating retraction;

FIG. 5A is an enlarged longitudinal cross-sectional view of the middle part of the first embodiment shown in FIG. 5 showing the needle retention chamber and the plunger seal taken in the position of FIG. 5 before retraction has occurred;

FIG. 5B shows a stop in the barrel seen along the lines 5B—5B of FIG. 5;

FIG. 5C is an alternate form of the stop of FIG. 5B showing that the stop can be a series of one or more radial projections;

FIG. 5D shows an alternate location of the stop of FIGS. 5B and 5C that can be helpful in setting a stroke for the syringe.

FIG. 6 is a longitudinal cross-sectional view of the syringe of the previous Figures with the needle retracted into the needle retention chamber and the handle in its full forward position with the thumb cap captured in an opening in the back of the syringe barrel;

FIG. 7 is a longitudinal cross-sectional view of FIG. 6 showing how the handle would separate from the needle retention chamber in the syringe of FIG. 6 if the handle is pulled back after the needle is retracted;

FIG. 8 is a longitudinal cross-sectional view of a second embodiment of the invention having a retractably mounted needle, a needle retention chamber, a stepped handle having a plurality of stepped serrations and a positive locking structure comprising a clip shown in a first position near the back of the handle;

FIG. 9 is a perspective view of an exemplary version of the clip as shown in FIGS. 8–14;

FIG. 10 is a longitudinal cross-sectional view of the syringe of FIG. 8 with the handle drawn back to draw fluid into the syringe thereby moving the clip to a second position nearer the front of the handle;

DETAILED DESCRIPTION OF THE INVENTION

Figure 11:
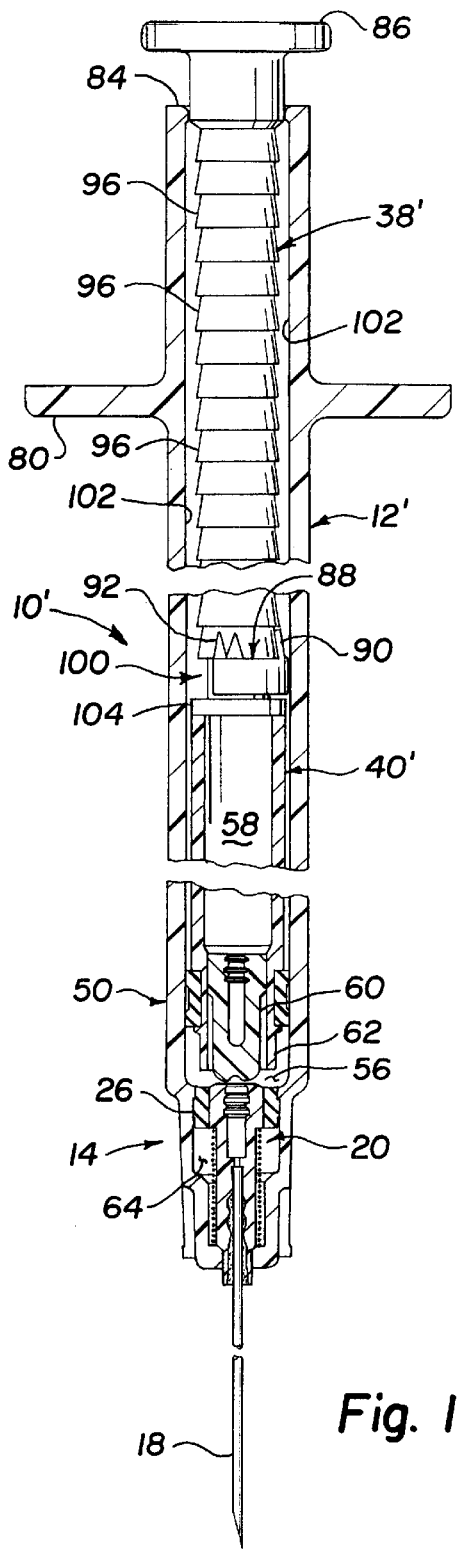
FIG. 11 is a longitudinal cross-sectional view of the retractable syringe of one-use of FIGS. 8 and 10 with the handle pushed fully forward to complete an injection.

In the description that follows, like parts will be referred to by the same reference numeral. The parts shown in the drawings are preferably circular or cylindrical in nature.

A retractable syringe of one use of the first embodiment is disclosed in FIGS. 1–7 in connection with the modification of a retractable syringe shown in FIGS. 1–3 of U.S. Pat. No. 5,632,733. While details of the preferred retractable syringe can be found in the cited reference as well as the other references listed in the background of the prior art herein, its main attributes will be briefly described here in connection with the present invention. The present invention provides a positive lock of the plunger handle to prevent reuse even if the syringe is not retracted after its first use. It is to be understood that the invention is not to be limited to the particular retraction device or structure and it could be used with other retractable needle devices, especially those which operate by pressing forward on the plunger handle after the injection is completed. There are a number of devices that retract the needle in a rearward direction into an opening in the plunger. For example, Toft, U.S. Pat. No. 5,407,436 or Pressly, Sr., U.S. Pat. No. 5,713,952 might be improved using the present invention. In the latter case, although the plunger handle does have a feature to discourage a second use, it functions only if the syringe is actually retracted.

The retractable syringe of one use of the present invention is generally referred to by the reference numeral 10 in FIG. 1. Syringe 10 has an elongated hollow syringe barrel 12 having a front end portion 14 and open back end portion 16. A retractable needle 18 is retractably mounted in a retraction structure 20 which includes an elongated needle holder 22 having a shoulder in front which rests at an opening 24 at the front of front end portion 14 to prevent forward movement. A small portion of the needle holder is seen extending forwardly beyond the barrel in FIG. 1. A separable retainer member 26 is a ring-like structure separably and frictionally engaged along an interface 28 with an enlarged head 30 of retainer member 26. The interface is oriented in the direction of retraction. Retainer member 26 together with head 30 of needle holder 20 are preferably press fit against the internal sidewall 32 of front portion 14 where they are held against the retracting force applied by compressed spring 34. Spring 34 has one end resting on a ledge at the front of portion 14 and a rear end pressing against the underside of head 30 of needle holder 22 without also pressing against the removable retainer member 26. Needle 18 is fixed in needle holder 22 by means of adhesive 36.

The syringe is operated by movable parts comprising a handle 38 removably attached to a needle retention chamber 40 by means of a detent connection 42 preferably forming a snap fit of the front part 44 of handle 38 with the back end of needle retention chamber 40. The handle 38 preferably has a core 76 with guide flutes 78 and a thumb cap 70 as seen in FIG. 2. Finger grips 80 operate in conjunction with thumb cap 70 to allow one handed operation. As seen in FIG. 7, front 44 of handle 38 has a groove 46 which removably mates with a single or multiple projections 48 at the back end of needle retention chamber 40 comprising a detent connection 42. The amount of force required to release the handle portion 38 from the portion 40 is less than the force required to pull the needle retention chamber past a stop in the barrel. The handle will separate from the needle retention chamber leaving the needle retention chamber in the barrel.

Movable parts 38, 40 together act as a movable plunger mounted for reciprocation in barrel 12 with a piston seal in sliding sealed contact with the interior of barrel 12. Needle retention chamber 40 has a front end portion 50 with piston seal 52 mounted thereon. Seal 52 is in sliding sealed contact with the interior surface 54 of barrel 12 thereby establishing a variable fluid chamber 56 below front end 50 of needle retention chamber 40. The needle retention chamber has an opening at its front end sealed with a removable plug member or other seal 60 which is preferably held in the opening by frictional engagement.

Needle retention chamber 40 has a retention space 58 to retain the retracted needle and the removable plug member 60 which slidingly seals the opening into chamber 58. The extreme front of front end portion 50 comprises a tip 62 which serves to contact and move retainer member 26 from head 30 into a space 64, below the head 30 of the needle holder, in the front end portion 14. This is accomplished automatically by depression of the handle (movable parts) from the full "end of injection position" shown in FIG. 4. Further depression of the handle from the FIG. 4 position of the movable parts removes the ring shaped retainer member and dislodges the plug member 60 thereby opening retention space 58 and releasing needle 18 for retraction into space 58, as illustrated in FIG. 6. The structure described so far provides a retracting needle syringe which prevents needle sticks and is not easily reused because the parts are disconnected from each other after retraction and the thumb cap is closely received into the open back 16 of the barrel 12. The present invention goes still further to make it impossible to reach the needle or other parts if the syringe is retracted and to prevent refilling if the syringe is not retracted.

Most significantly the inner surface 54 of syringe barrel 12 is provided with positive locking structure 66 which comprises radially inwardly projecting constriction or constrictions designed to limit movement of needle retention chamber 40 in a rearward direction and prevent its removal from the syringe barrel after one use. Needle retention chamber 40 preferably has an enlarged rear end 68 which cooperates with the positive locking structure 66 on the inside of the syringe barrel. Its clearance is such that it can be forced past locking structure 66 in a forward direction by thumb force on thumb cap 70. However, once the syringe handle 38, 40 is pushed forward to pass back end 68 of needle retention chamber 40 past constriction 66, any attempt to reverse this traverse cannot be accomplished because handle portion 38 will separate from the retention chamber portion 40 as shown in FIGS. 5 and 7.

FIG. 1 shows the position of the syringe in the ready-to-fill position. The handle 38, 40 has been depressed to bring the back end of the needle retention chamber into contact with what will be called a first stop 66 comprising a constriction of the barrel diameter at a fixed location inside the barrel. The back end 68 of needle retention chamber 40 preferably comprises what will be referred to as a second stop which cooperates with the first stop to prevent further forward movement of the movable parts unless noticeable force is applied. The second stop is preferably a diametrical enlargement of the cylindrical needle retention chamber most appropriately located as indicated in FIG. 1 at the back of the needle retention chamber. However, the diametrical enlargement could be moved forward from the back end of the needle retention chamber as geometry requires. A reason for a different location of the diametrical enlargement on the needle retention chamber would be to vary the filling stroke to establish different fill volumes for different dosages. The first and second stops 66, 68 comprise positive locking structure. Although the variable fluid chamber 56 in the ready-to-fill position appears rather large, in reality it is only a relatively small portion of the maximum syringe volume and very small in absolute terms for a 1 cc or ½ cc syringe. As will be seen, the location of stop 66 and the length and diameter of chamber 40 and barrel 12 will determine the fill volume. The needle retention chamber is sized and positioned to receive the entirety of needle 18 so that no sharp tip is exposed after retraction.

FIG. 3 represents the next step in the filling process whereby the user is free to pull the syringe handle back until a catch 72 on the front end of the needle retention chamber 40 catches on the first stop 66. This provides the user with a tactile feel to indicate that the syringe has been fully filled with injection fluid.

FIG. 4 illustrates the next step in the syringe operation whereby the needle has been inserted into a patient (not shown) and the plunger depressed to the end-of-injection position. Here the front end portion of the needle retention chamber 40 is positioned such that forward movement of tip 62 can sequentially begin removing the plug member 60 from the opening of needle retention chamber 50 and sliding the retainer member 26 off the head 30 of the needle holder 22 of retraction structure 20. This is accomplished by pressing on thumb cap 70 until thumb cap 70 is closely received in an opening 74 in the enlarged back end 16 of barrel 12. This becomes the retracted needle position of FIG. 6 wherein the retractable needle has been retracted into the needle retention chamber along with the plug member before it. Thumb cap 70 has been received in opening 74. In this position the needle is safely retracted and the handle neatly tucked into the open back of the syringe barrel to prevent reuse.

If, however, the user refuses to retract the syringe after the position of FIG. 4 is reached, we do not proceed to FIG. 6 but rather to FIG. 5. FIG. 5 shows that an attempt to remove the movable parts by pulling on handle portion 38 merely results in the second stop 68 preferably located at the back of needle retention chamber 40 contacting first stop 66 where it can go no further. Handle portion 38 simply separates from the needle retention chamber 40 by release of the detent connection 42 leaving no access to the internal parts of the syringe. The groove 46 in the front 44 of handle 38 disengages the protrusion or protrusions 48. Slight distortion of the parts may occur during the release. As can be seen in FIGS. 4 and 5, there would be inadequate fill volume in the variable chamber to reuse the syringe even if the handle portion 38 were reinserted into the back of the barrel.

FIG. 5A is an enlargement of the middle section of FIG. 5 between the break lines shown in FIG. 5. Here the catch 72 is seen in greater detail as preferably an annular tooth-shaped radial protrusion on the front end portion 50. The back end portion 68 of needle retention chamber 40 may have an enlarged diameter surface 82 having edges which come up against first stop 66. Detent protrusions 48 are seen at the back end of needle retention chamber 40 which fits groove 46 seen in FIG. 5 of handle portion 38 which has been removed. FIG. 5B is a cross section showing the first stop 66 can be a continuous constriction around the internal diameter of barrel 12. FIG. 5C shows that the stop 66 could be a plurality of enlarged areas or inwardly radially projecting portions positioned to contact and lock the back end 68 of needle retention chamber 40 thus preventing it from being removed by handle 38. Similarly, if lock 66 is continuous, the back end of needle retention chamber 40 comprising second lock 68 could be discontinuous. One or the other should be continuous so that there is no angular orientation of the needle retention chamber which will allow it to be pulled out of the barrel by the handle.

FIG. 5D illustrates that the back end of the needle retention chamber 40 can be modified as a straight back end portion 68' in FIG. 5D which is sized to fit through the opening in the constriction caused by stop 66. Alternately, a diametrically enlarged portion 69 on the outside of needle retention chamber 40 can be located at a different axial position to serve as an abutment against which the positive lock 66 works. The diametrically enlarged portion 69 can be considered the second stop which cooperates with first stop 66 to limit rearward movement of the needle retention chamber. Second stop 69 operates in exactly the same way as the enlarged back end portion 68 of needle retention chamber 40 in previous Figures in that it can be forced through the opening in the constriction 66 when moving in a forward direction in response to force applied to the thumb cap 70. When the user attempts thereafter to pull the handle back, diametrically enlarged portion 69 comes into contact with constriction 66 and requires a pulling force which is greater than the force required to separate handle 38 from needle retention chamber 40. This is simply an alternate way of providing a different movement of the handle relative to the barrel which may be useful in setting the stroke of a particular syringe to deliver a desired dose.

FIGS. 8–14 represent a second embodiment of the retractable syringe of one use having the preferred retraction mechanism disclosed in the previous figures, for which the same reference numerals will be applied. Modifications from the parts shown in the previous disclosure will be indicted by the use of primes. The syringe of the second embodiment is generally referred to by the reference numeral 10'. Retractable syringe 10' has exactly the same retractably mounted needle 18 and retraction structure 20 of the first embodiment. It has a syringe barrel 12' which varies from the first embodiment in that it does not have the same positive locking structure and does not have the enlarged back end portion 16. Syringe barrel 12' does have a front end portion 14 and an open back 84. A movable handle is reciprocatably mounted in the syringe barrel 12' comprising a needle retention chamber 40' attached to a handle portion 38'. The front end portion 50 of the movable handle includes the same piston seal 52 and slidably removable plug member 60 as in the first embodiment already discussed. The back end portion of the movable handle has a cap member 86 comprising a thumb cap at the back end of the handle for applying thumb force to the handle. The needle retention chamber 40' is either attached or removably attached to the handle portion 38', but only for purposes of manufacture. If these two parts of the movable member are made separately, they are joined in such a way that they cannot be separated as by welding, gluing or other permanent fixation or preferably be molded as one movable handle.

The second embodiment differs from the first embodiment in that the positive locking structure is a preferably metal clip 88 shown in FIG. 9. Clip 88 has a tab 90 and one or more pairs of locking teeth 92 on a body 94. Tab 90 is slightly bent inwardly to cooperate with a plurality of stepped serrations 96 extending along the handle portion of the movable parts behind the needle retraction chamber 40'.

FIG. 8 illustrates the starting position of the retractable syringe of one use of the second embodiment. In the starting position, the movable handle is pushed forward fully in the syringe body to lightly touch the retraction mechanism 20 without causing retraction. This is easily done by means of a tactile feel by the operator who touches the plug member 60 in this case against the needle holder head 30. The positive locking structure 88 is carried by the handle portion 38' and is movable from a first position 98 in FIG. 8 to a second position 100. This is accomplished by the simple expedient of pulling the movable handle back relative to the syringe barrel. The positive locking structure comprising clip 88 is movable only in one direction from the first position near the back of the handle to the second position nearer the front of the handle. The points 92 are designed to engage the inner surface 102 of barrel 12' if an attempt is made to move the clip rearwardly with the handle. Because the points 82 are pointed backwardly, they are free to slide along the interior surface 102 when the clip is moving forward in the barrel. Tab 92 will ride over the edges of the serrations 96 when the handle is moving rearwardly relative to clip 88 so when the handle is pulled back, the stepped serrations simply slide relative to the clip and the clip can be located at the second position 100 of FIG. 10 from the first position 98 of FIG. 8. FIG. 10 illustrates the position of the handle relative to the clip 88 after the maximum amount of fluid has been drawn into the fluid chamber 56 through needle 18. The needle retention chamber 40' is located just forward of the second position of the locking structure 88. Thus, it is seen that the clip comprising a locking structure.

FIG. 11 shows the position of the movable handle at the end-of-injection position after all the fluid has been expelled from variable chamber 56. It can be seen that the inwardly angled tab 90 of clip 88 catches the underside edge of a serration 96 to move forward with the movable handle 38', 40'. The backwardly angled points 92 simply slide along the interior surface of the syringe barrel 12' without interfering with the forward motion of the movable handle.

Figure 12:
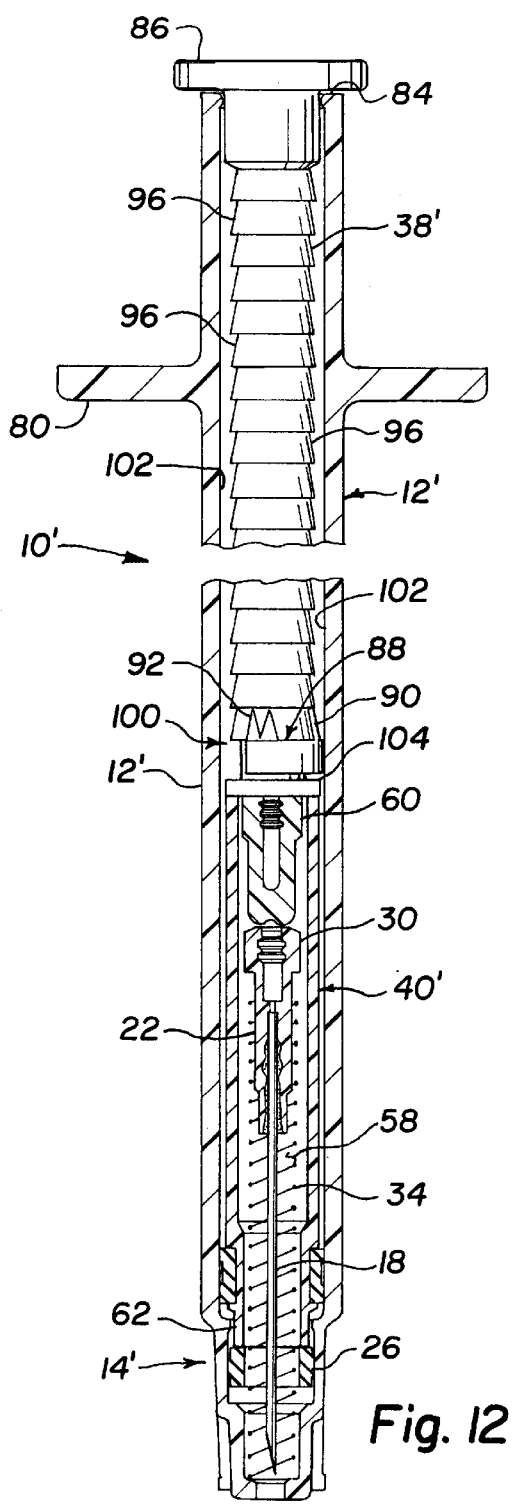
FIG. 12 is a longitudinal cross-sectional view of the syringe of FIG. 11 with the handle pushed forward to the maximum extent beyond a full injection position, causing the needle to retract into the needle retention chamber.

FIG. 12 illustrates how the syringe 10' of the second embodiment has its needle retracted by simply pushing on the thumb cap 86 and moving the movable handle from the end-of-injection position of FIG. 11 to the retracted position of FIG. 12. It can be seen that the retainer ring 26 has been removed from head 30 of needle holder 22 by tip 62 into the space 64 and the spring loaded needle holder and needle move rearwardly as the plug member is removed from the front end portion of the needle retention chamber 40' and retracted into the chamber and held there by means of spring 34. The parts are sized so that the entire needle including the sharp point is withdrawn into the barrel 12'. What has been described is locking structure located inside the barrel which has no affect on one rearward movement and one forward movement of the movable handle. Now, however, the positive locking structure 88 is located in the second position in FIG. 12. Any reverse movement of the needle retention chamber in a rearward direction is limited by the clip 88 because the sliding points 92 are now positioned to dig into the interior surface 102 of barrel 12' thereby preventing rearward movement of the handle by contact of the bottom of the clip 88 with the back end 104 of needle retention chamber 40'. Since the clip cannot move in a rearward direction and blocks rearward movement of the needle retention chamber 40', it is seen that the handle 30 cannot be removed from the syringe after one use. By comparing the position of the clip in FIGS. 11 and 12 it can be recognized that it does not matter whether the syringe is retracted or not, the movable handle still cannot be removed. Therefore the handle is positively locked into the syringe after one use. It might also be evident that the filling volume can be adjusted depending upon the initial position of the clip 88 with respect to the handle portion 38' as explained in Shonfeld et al, U.S. Pat. Nos. 5,531,691 and 5,562,623 which were mentioned in the background of the prior art.

Figure 13:
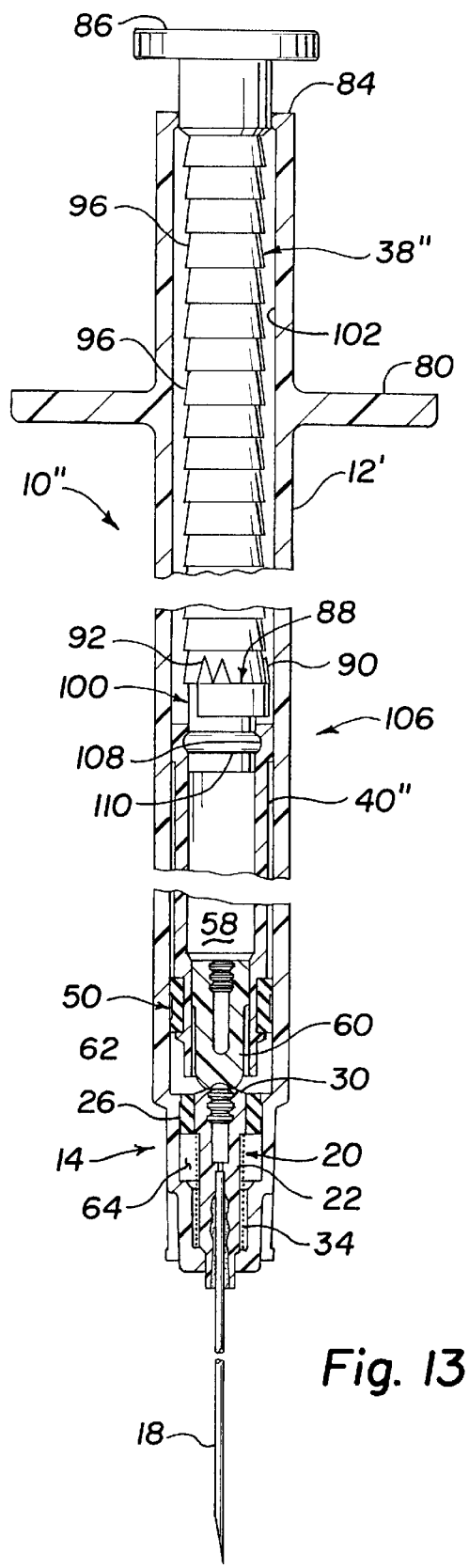
FIG. 13 is a longitudinal cross-sectional view of an alternate construction of the second embodiment of the invention wherein the handle is separably affixed to the back of the needle retention chamber in a manner similar to that of the first embodiment, with the plunger in the full end of injection position.
Figure 14:
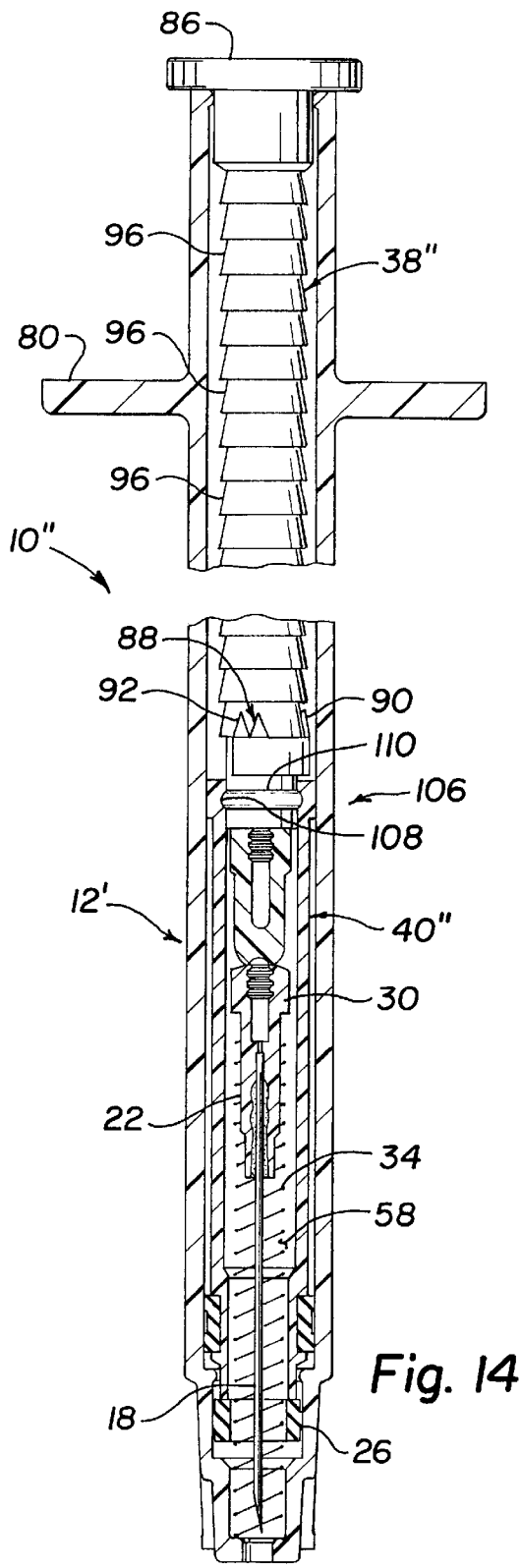
FIG. 14 is the syringe of FIG. 13 wherein the plunger has been pushed further forward from the position of FIG. 13 to retract the needle into the needle retention chamber.

FIGS. 13 and 14 correspond respectively to FIGS. 11 and 12. They syringe 10" differs from the syringe 10' of FIGS. 11 and 12 only in that the handle 38" is releasably connected to the needle retention chamber 40" by a releasable connection 106. The back end portion of needle retention chamber 40" has a groove 108 which is preferably a circumferential groove and the front end of handle portion 38" has a preferably circumferential radial projection 110 in the form of a raised area fixed to the front end portion of handle portion 38" which fits into groove 108. Releasable connection 106 makes the movable parts comprising the handle portion 38" and the needle retention chamber 40" a two part structure which facilitates molding and assembly and makes it possible to vary one of the parts while the other releasable part remains a standard size. For example, the handle portion could be made longer or shorter and used with the same needle retention chamber or the needle retention chamber could be varied in length while using a standard handle portion 38'. One reason to vary the needle retention chamber may be the use of needles of different length. It is also another way of varying the stroke to vary the maximum dose. The length of the barrel could be altered but the length of the barrel is not critical because the clip 88, operating in exactly the same way as previously described with respect to FIGS. 8–12, prevents the handle 38" and needle retention chamber 40" from being withdrawn after the first injection is made. The handle is prevented from being withdrawn whether or not the retraction mechanism 20 is activated.

Figure 15:
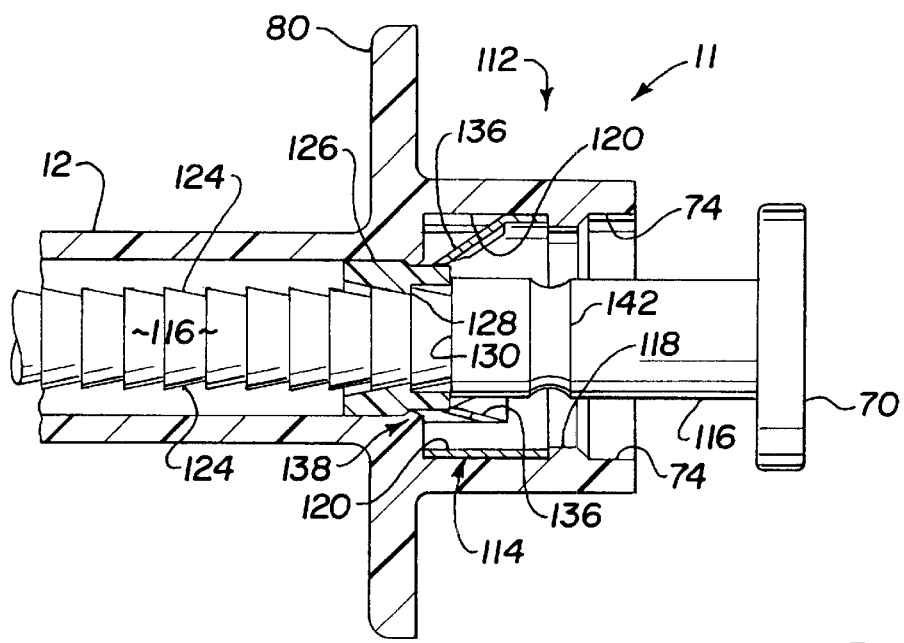
FIG. 15 is a longitudinal cross-sectional view of a third embodiment of the invention having the same retractable needle and needle retention chamber as the previous Figures but showing a different positive locking structure which allows the handle to be pulled back one time to fill the syringe.
Figure 16:
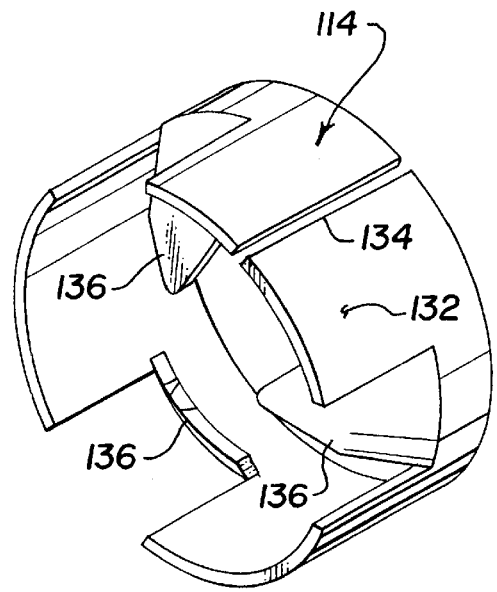
FIG. 16 is a perspective view of the springing clip of FIG. 15 showing a preferred plurality of springing points.

FIGS. 15–19 represents a third embodiment of the invention which will be referred to as syringe 11. Syringe 11 is preferably the retracting syringe of FIGS. 1–7 with certain exceptions to be enumerated below. The parts that are not shown in FIGS. 15–19 are to be considered identical to those of the first embodiment up to the back end of the needle retention chamber. The back end portion 112 of barrel 12 has been modified to accept a springing clip structure 114 which is shown in FIG. 16. The barrel has a widened back end behind the finger grips 80 much like the back 16 of the first embodiment. It still has the opening 74 to captively receive the thumb cap 70 at the back of handle 116 but has a constricting abutment surface 118 just forward of the opening 74. Abutment 118 forms a groove 120 around the enlarged back end portion 112 of barrel 12 wherein springing clip 114 is received in a fixed position relative to the barrel. As will be seen, springing clip 114 comprises structural located inside the barrel that limits subsequent movement of the needle retention chamber in a rearward direction after a first use of the syringe.

Handle 116 extends behind a needle retention chamber 122 (FIG. 17) and is serrated along its length by a plurality of stepped serrations 124 which are like the stepped serrations 96 of the second embodiment. A sliding part in the form of collar 126 is carried by handle 116. Collar 126 includes a catch 128 adapted to catch an edge 130 of any stepped serration 124. It may be a circular part or a split circular part to aid in mounting the collar onto the handle. Thumb cap 70 could be installed and fixed in place after the collar is installed on the shaft of the handle 116 or the handle could be two parts.

Figure 17:
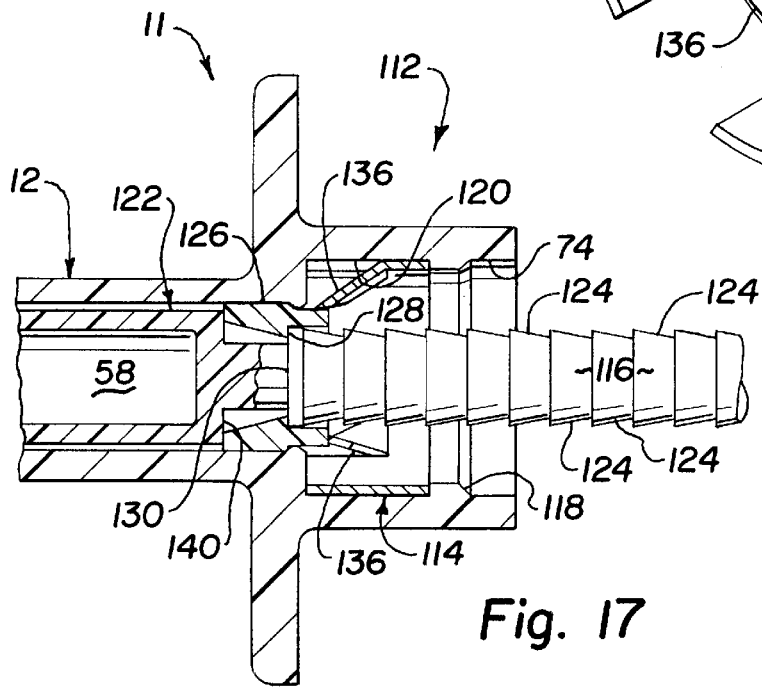
FIG. 17 is a longitudinal cross-sectional view showing the third embodiment of FIG. 15 after the handle is pulled back to a position corresponding to that of the embodiment of FIG. 10.

Springing clip 114 preferably has a circular body 132 and a gap 134 which enables slight compression of the circular body to allow it to be inserted into groove 120, passing over abutment 118. Springing clip 114 has a plurality of springing teeth 136 which are initially separated from the handle by a rear end portion of sliding collar 126 as seen in FIG. 15. This is the initial position of the handle which corresponds to the starting position of FIG. 1 or FIG. 8. A slight constriction 138 in the handle 12 prevents collar 126 from moving rearwardly as the handle 116 is pulled back to the position of FIG. 17, thereby drawing fluid into the variable fluid chamber 156 (not shown) as in FIG. 3. The serrations and catch are slightly exaggerated in the drawings for illustration but allow the handle to be pulled back without difficulty to the ready-to-inject position of FIG. 17. This represents a first withdrawal of the handle 116 and needle retention chamber 122. The back end of needle retention chamber 122 has a stop surface 140 which comes up against collar 126 when the handle is fully withdrawn, as shown in FIG. 17. Collar 126 is still keeping springing teeth 136 from contacting the handle in FIG. 17.

Figure 18:
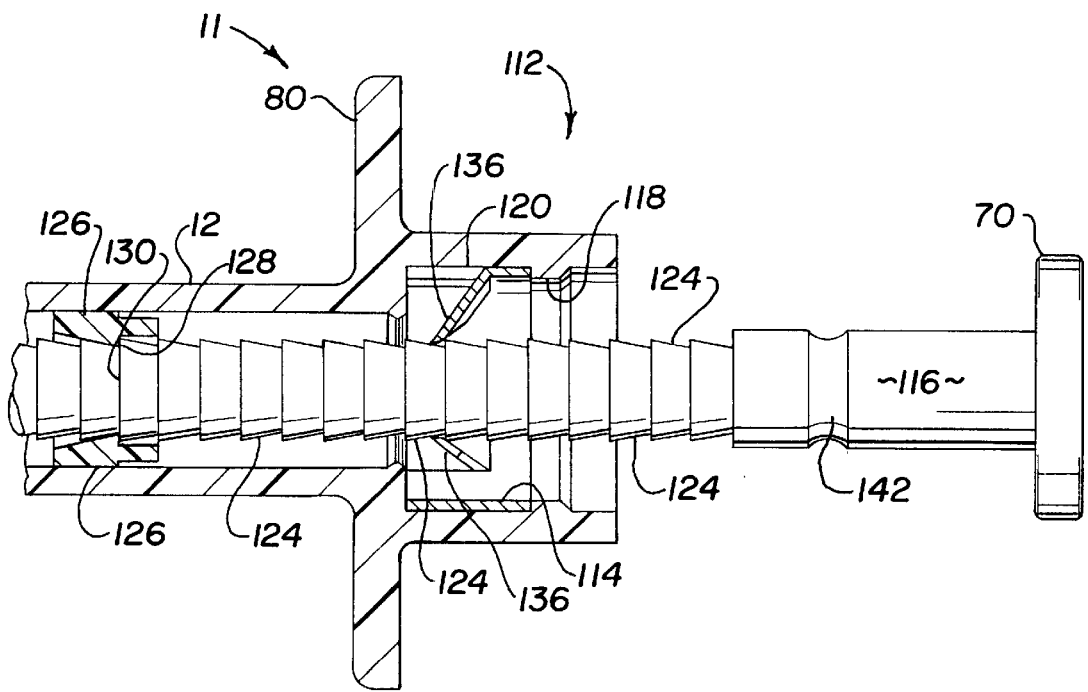
FIG. 18 is a longitudinal cross-sectional view showing how the springing clip is released to engage the handle as soon as the handle begins to move forward during an injection and thereby prevent any significant rearward movement of the handle.
Figure 19:
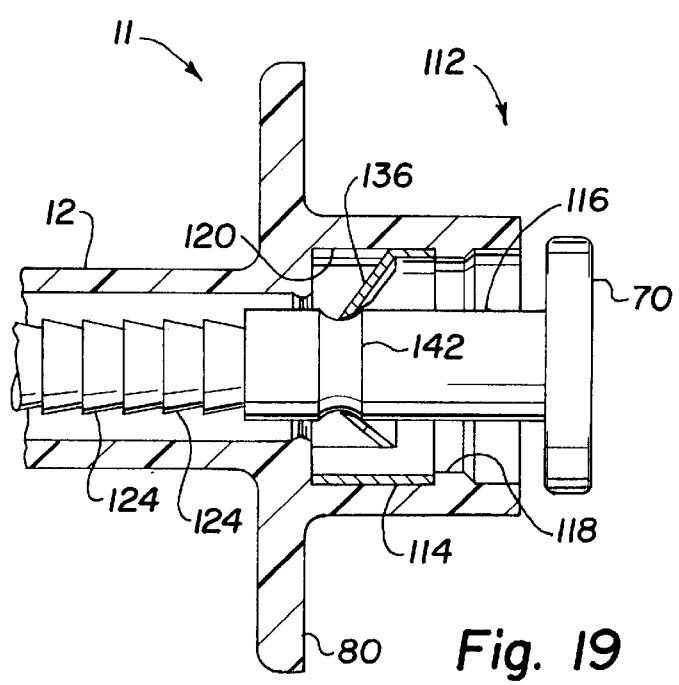
FIG. 19 is a longitudinal cross-section of the syringe of the third embodiment shown in FIG. 18 after the handle has been pushed forward to the completion of injection position.

FIG. 18 shows what happens when the handle 116 of syringe 11 starts moving forward in response to thumb force on cap 70 from the position in FIG. 17 to the position of FIG. 18 and ultimately to the position of FIG. 19. What happens is that catch 128 of sliding part or collar 126 catches an edge 130 on a stepped serration 124 to move forward away from springing clip 114. This allows springing teeth 136 to ride over stepped serrations 124 as handle 116 is being moved forward. This continues until the position of FIG. 19 is reached.

FIG. 19 illustrates the end-of-injection position with the rest of the parts corresponding to the position of FIG. 4 or FIG. 13. The front end portion of the needle chamber 50 like FIG. 1 has reached the retraction mechanism 20 in the front of the syringe, and the fluid has been expelled through needle 18. The springing teeth reside in a groove 142 in the back end portion of 116. However, it should also be recognized from the sharp angle of the teeth 136 relative to stepped serrations 124 that it is impossible to pull the handle 116 back from the position of FIG. 18 or any intermediate position between the position of FIG. 15 and the position of FIG. 19, because the springing teeth will dig into any adjacent stepped serration and jam the handle in the barrel. Therefore, springing clip 114 provides a positive locking structure located inside the barrel in a fixed position to engage the movable parts which has no affect on one rearward movement and one forward movement of the movable parts (handle and needle retention chamber) to the fullest extent of forward movement, but subsequent movement of the needle retention chamber in a rearward direction is limited to maintain said chamber within the syringe barrel because the handle cannot be drawn back a second time.

Finally, from the position of FIG. 19 a final push on the thumb cap 70 in the forward direction after the completion of injection position of FIG. 19 results in the retraction operation of the retractable parts by movement of the handle as indicated in FIGS. 6, 12 and 14. The needle is retracted into the needle retention chamber 122 and contained within the barrel. Thus the plunger activated retraction and retraction mechanism may be the same in all three embodiments with different positive locking structure provided to limit rearward movement of the needle retraction chamber.

In the best mode, the parts are made from conventional injection moldable plastic, normally polypropylene. The piston seal is conventional and the clips are preferably metal.

Although illustrative embodiments of the present invention have been described herein with reference to the accompanying drawings, it is to be understood that the invention is not limited to those precise embodiments, and that various other changes and modifications may be effected therein by one skilled in the art without departing from the scope of spirit of the invention.

What is claimed:

1. A retracting syringe of one use having a handle operated needle retention chamber which cannot be removed from the syringe barrel, comprising:

an elongated hollow syringe barrel having a front end and an open back;

a retractable needle retractably mounted in a retraction structure located in the front end of the syringe barrel and biased for retraction in a rearward direction;

movable parts comprising a handle attached to the needle retention chamber sealingly and slidably mounted for movement in the syringe barrel by means of the handle extending from the open back of the barrel, the needle retention chamber having an openable sealed opening in front to receive the retracted needle;

retraction of the needle into the needle retention chamber being triggered by forward movement of the needle retention chamber against the retraction structure in response to movement of the handle after an injection is completed;

positive locking structure located within the syringe barrel to limit movement of the needle retention chamber in a rearward direction and prevent its removal from the syringe barrel after one use;

whereby the retracted needle after use is safely contained in the needle retention chamber within the syringe barrel and cannot be easily removed by manipulation or withdrawal of the handle.

2. The retracting syringe of one use of claim 1 wherein the needle retention chamber is attached to the handle.

3. The retracting syringe of one use of claim 1 wherein the needle retention chamber is removably attached to the handle.

4. The retracting syringe of one use of claim 1 wherein the positive locking structure comprises structure located inside the barrel to engage the movable parts, which is adapted to have no effect on one rearward movement and one forward movement of the movable parts to the fullest extent of forward movement but subsequent movement of the needle retention chamber in a rearward direction is limited to maintain said chamber within the syringe barrel.

5. The retracting syringe of one use of claim 4 wherein the structure located inside the barrel that limits said subsequent movement of the needle retention chamber in a rearward direction remains at a fixed location with respect to the barrel during use of the syringe.

6. The retracting syringe of one use of claim 5 wherein the structure inside the barrel that remains at a fixed location with respect to the barrel comprises a constriction of the barrel diameter comprising a first stop while the needle retention chamber has a diametrically enlarged section comprising a second stop wherein the second stop can be forced past the first stop in a forward direction by pressing on the handle but which resists movement in a rearward direction caused by pulling on the handle.

7. The retracting syringe of one use of claim 6 wherein the handle is removably attached to the needle retention chamber and separable therefrom by a separation force which is less than the force required to force the second stop past the first stop in a rearward direction and therefore separates leaving the needle retention chamber inside the barrel.

8. The retracting syringe of one use of claim 7 wherein the handle is separable from the needle retention chamber by release of the separating parts without breaking them.

9. The retracting syringe of one use of claim 8 wherein the needle retention chamber has a front end portion carrying a catch which can be forced forward past the first stop by pressing on the handle before the second stop moves past the first stop, the catch limiting the amount of rearward travel of the movable parts to establish the maximum design fill volume of the syringe.

10. The retracting syringe of one use of claim 5 wherein the structure located inside the barrel that limits subsequent movement of the needle retention chamber in a rearward direction by remaining at a fixed location comprises a structure mounted inside the open back of the barrel.

11. The retracting syringe of one use of claim 5 wherein said structure comprises a springing clip which positively engages the handle after the handle is pushed forward to complete an injection and thereby prevents the handle from being subsequently withdrawn in a rearward direction once the handle is engaged by the clip.

12. The retracting syringe of one use of claim 11 wherein the handle includes a thumb cap for pushing the handle forward, the thumb cap being closely received in the open back of the barrel when retraction of the needle is triggered by full depression of the plunger.

13. The retracting syringe of one use of claim 11 wherein the handle extending behind the needle retention chamber is serrated along its length and includes a sliding part on the handle which initially separates the springing clip from the handle allowing the plunger to be drawn back to fill the syringe with fluid and thereafter is moved forward when the handle is depressed thereby releasing the spring clip for contact with the handle.

14. The retracting syringe of one use of claim 5 wherein said structure located inside the barrel that limits subsequent movement of the needle retention chamber in a rearward direction comprises a springing clip mounted inside the open back of the barrel in a fixed position and a sliding part in contact with the handle, the sliding part holding the springing clip away from the handle when the handle is withdrawn in a rearward direction and releasing the springing clip to contact the handle by moving forward with the handle when the handle is moved forward in the barrel.

15. The retracting syringe of one use of claim 4 wherein the structure inside the barrel that limits said subsequent movement of the needle retention chamber in a rearward direction varies its position with respect to the barrel during use of the syringe.

16. The retracting syringe of one use of claim 15 wherein said structure comprises a springing clip which positively engages the handle after the handle is pushed forward to complete an injection and thereby prevents the handle from being subsequently withdrawn in a rearward direction once the handle is engaged by the clip.

17. The retracting syringe of one use of claim 15 wherein the handle includes a thumb cap for pushing the handle forward, the thumb cap being closely received in the open back of the barrel when retraction of the needle is triggered by full depression of the plunger.

18. In a syringe of one use having a syringe barrel having a needle for injection of fluid extended from the front of the barrel and a movable handle extending from the back of the barrel, mounted for limited reciprocation in the barrel, the movable handle including a front end portion having a piston in sliding sealed contact with the interior of the barrel wherein the piston establishes a variable fluid chamber for injection fluid in the barrel, a back end portion of the handle having a thumb cap for applying thumb force to the handle and positive locking structure in the barrel which limits a second rearward movement of the handle after a first rearward movement of the handle to fill the variable fluid chamber with injection fluid and a first forward movement of the handle to inject the fluid, the improvement comprising:

the needle is a retractable needle mounted in a retraction structure in the front of the barrel with the needle extended in its unretracted position and biased for retraction in a retraction direction;

the front end portion of the handle is adapted to operate the retraction structure to retract the needle, the front end portion having a needle retention chamber and said piston behind the variable fluid chamber to receive the retracted needle;

the needle retention chamber having a front end and a diametrically enlarged section;

the positive locking structure is a stop positioned to limit rearward movement of needle retention chamber to within the confines of the barrel by contact with said enlarged section of the needle retention chamber;

the handle is a two part handle having a back end portion which separates from the front end portion if the needle retention chamber is attempted to be pulled past the stop by pulling on the back end portion of the handle; and wherein the syringe is not subject to reuse even if the needle is not retracted after use.

19. The syringe of one-use of claim 18 wherein said stop is formed as a construction in the barrel which allows the front end portion of the handle and the needle retention chamber to be moved forward of the stop by pressing on the thumb cap; and if the needle retention chamber is pulled back it contacts the stop when moving in a rearward direction, and generates a resisting force which is greater than the force required to cause separation of the handle thereby ensuring that the needle will be retained within the barrel thereby preventing a second use of the syringe.

20. The retracting syringe of one use of claim 19 wherein the handle is separable form the needle retention chamber by release of the separating parts without breaking them.

21. The syringe of one use of claim 19 wherein the rear end portion of the handle and the needle retention chamber are separably connected by means of a snap fit.

22. The syringe of one-use of claim 19 wherein the needle retention chamber carries a catch near the front end which can be forced forward past the stop by pressing on the handle, the catch being adapted to come back against the stop when the handle is pulled back to establish the maximum size of the variable fluid chamber.

23. A retracting syringe of one use having an operating handle which cannot be removed from the syringe barrel after one use, comprising:

an elongated hollow syringe barrel having a front end and an open back;

a retractable needle retractably mounted in a retraction structure located in the front end of the syringe barrel and biased for retraction in a rearward direction;

a movable handle in the syringe barrel having a front end portion having a piston in sliding sealed contact with the interior of the barrel, a back end portion having a cap at the back end for applying thumb force to the handle, and a needle retention chamber in the front end portion of the handle for receiving the retractable needle;

positive locking structure located within the syringe barrel to limit movement of the handle in a rearward direction and prevent its removal from the syringe barrel after one use;

whereby the retracted needle after use is safely contained in the needle retention chamber within the syringe barrel and cannot be removed by manipulation or withdrawal of the plunger.

24. The retracting syringe of one use of claim 23 wherein the handle carries the positive locking structure which is movable in only one direction from a first position near the back of the handle to a second position nearer the front of the handle, the locking structure being adapted to positively engage the syringe barrel and limit movement of the needle retention chamber in a rearward direction after the locking structure is moved forward of the first position.

25. The retracting syringe of one use of claim 24 wherein the needle retention chamber is located just forward of the second position of the locking structure.

26. The retracting syringe of one use of claim 25 wherein the needle is retracted by thumb pressure exerted on the cap at the back of the plunger after the plunger is fully depressed to make an injection.

27. The retracting syringe of one use of claim 25 wherein the back end portion of the handle has a plurality of stepped serrations and the positive locking structure comprises a clip having an inwardly angled tab relative to the stepped serrations which allows the clip to move forwardly while preventing the clip from moving rearwardly, the clip having at least one outwardly angled point which engages the syringe barrel to prevent withdrawal of the handle.

28. The retracting syringe of one use of claim 27 wherein the clip circumscribes part but not all of the stepped serrations on the back end portion of the handle.

29. The retracting syringe of one use of claim 23 wherein the positive locking structure located within the syringe barrel to limit movement of the handle in a rearward direction comprises a structure mounted in a fixed position relative to the barrel.

30. The retracting syringe of one use of claim 29 wherein said structure is located inside the open back of the barrel.

31. The retracting syringe of one use of claim 30 wherein the handle includes a thumb cap for pushing the handle forward, the thumb cap being closely received in the open back of the barrel when retraction of the needle is triggered by full depression of the plunger.

32. The retracting syringe of one use of claim 30 wherein said structure mounted inside the open back of the barrel in the fixed position relative to the barrel is a springing clip having one or more forwardly angled points which are protected by a sliding collar carried by the handle from contacting the handle during an initial withdrawal of the handle to draw fluid into the barrel to allow one withdrawal of the handle in a rearward direction from an initial forward position relative to the barrel, the sliding collar thereafter moving forward out of contact with the springing clip when the plunger is depressed to make an injection whereupon the springing clip engages the handle to prevent its withdrawal.

33. The retracting syringe of one use of claim 32 wherein the back end portion of the handle has a plurality of stepped serrations on which the sliding collar carried by the handle resides, the sliding collar having an angled surface which allows the plunger handle to move rearwardly relative to said collar, and the sliding collar being moved forward with the handle by engagement of said surface with one of the serrations on the handle.

34. A syringe of one-use, comprising:

an elongated hollow syringe barrel having a front end portion and an open back end;

a needle mounted in the front end portion of the barrel;

a two part movable handle mounted for reciprocation in the barrel, the handle having a head portion in front having a piston in sliding sealed contact with the interior surface of the barrel and a handle portion releasably connected to the head portion;

a lock mounted in the barrel that allows said head portion to pass the lock when the head and handle portion are inserted into said open back and a force is applied to the handle portion in a forward direction;

the handle portion being separated from the head portion when the handle portion is pulled back after having passed the lock in a forward direction, said separation occurring by release of the handle portion from the head portion due to resistance of the lock without breaking of the separating parts.

35. The syringe of one-use of claim 34 wherein said needle is a retractable needle retractably mounted in the front end portion of the barrel.

* * * * *